(12) United States Patent
Razzetti et al.

(10) Patent No.: US 8,063,244 B2
(45) Date of Patent: Nov. 22, 2011

(54) PROCESS FOR THE SYNTHESIS OF PREGABALIN

(75) Inventors: Gabriele Razzetti, Sesto San Giovanni (IT); Pietro Allegrini, San Donato Milanese (IT); Dario Pastorello, Milan (IT)

(73) Assignee: Dipharma Francis S.r.l., Baranzate (MI) (IT)

( * ) Notice: Subject to any disclaimer, the term of this patent is extended or adjusted under 35 U.S.C. 154(b) by 27 days.

(21) Appl. No.: 12/770,044

(22) Filed: Apr. 29, 2010

(65) Prior Publication Data

US 2010/0292506 A1   Nov. 18, 2010

(30) Foreign Application Priority Data

May 7, 2009   (IT) .............................. MI2009A0773

(51) Int. Cl.
C07C 229/00   (2006.01)
C07B 53/00   (2006.01)
(52) U.S. Cl. ....................... 562/553; 562/606
(58) Field of Classification Search ........................ None
See application file for complete search history.

(56) References Cited

U.S. PATENT DOCUMENTS

| 5,637,767 A | 6/1997 | Grote |
| 6,197,819 B1 | 3/2001 | Silverman |
| 6,359,169 B1 | 3/2002 | Silverman |
| 2005/0283023 A1 | 12/2005 | Hu |

FOREIGN PATENT DOCUMENTS

| EP | 1992609 A1 | 11/2008 |
| WO | WO 2008/009897 A1 * | 1/2008 |

OTHER PUBLICATIONS

Hoekstra et al., "Chemical Development of CI-1008, an Enantiomerically Pure Anticonvulsant", Organic Process Research & Development, 1997, 1: pp. 26-38.

* cited by examiner

*Primary Examiner* — Paul A Zucker
(74) *Attorney, Agent, or Firm* — Rothwell, Figg, Ernst & Manbeck, P.C.

(57) ABSTRACT

A process for the preparation of a compound of formula (I) is disclosed,

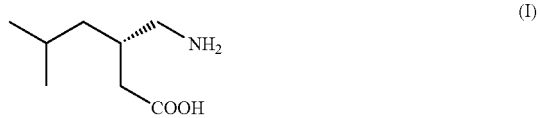

which comprises:
a) the reaction of a compound of formula (II)

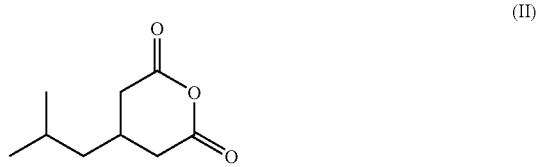

Figure 1:
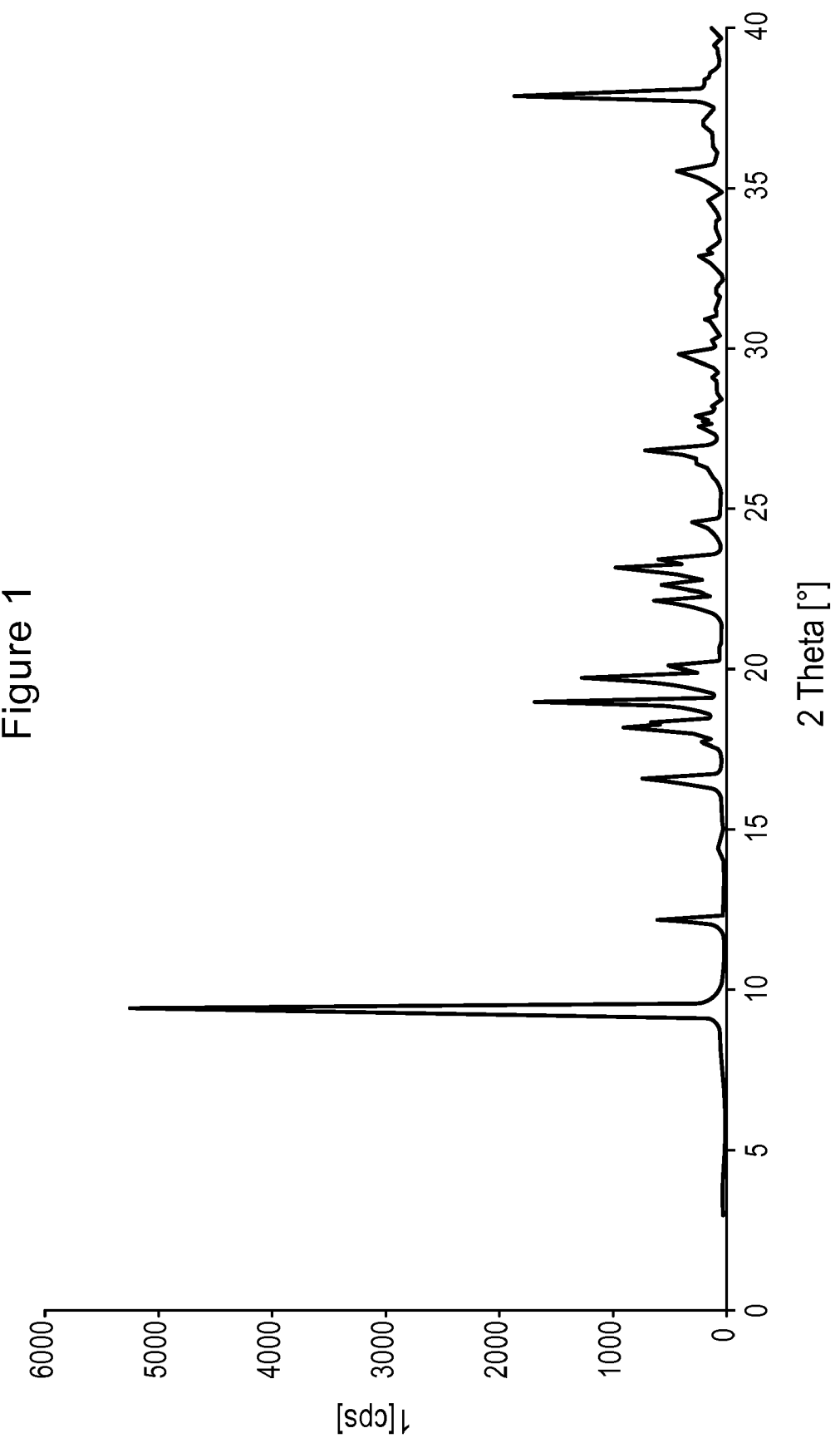

with zinc azide of formula (III)
$Zn(N_3)_2$   (III)
in the presence of a solvent of formula $R_1$—OH, wherein $R_1$ is herein defined, to obtain a compound of formula (IV),

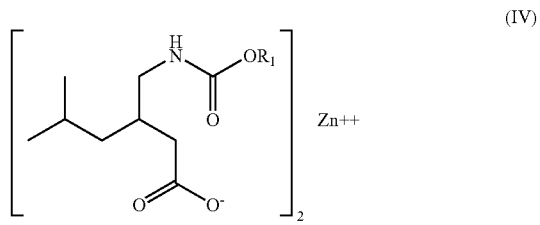

b) its conversion into a compound of formula (V);

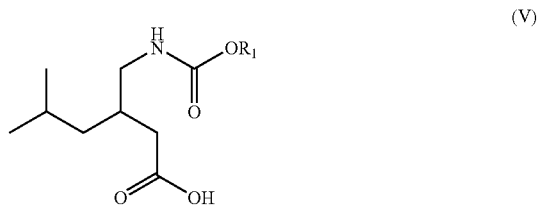

c) its enantiomeric enrichment to obtain the (S) enantiomer of formula (VI); and

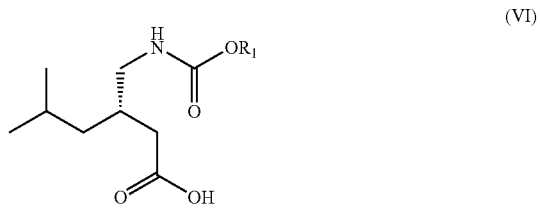

d) the hydrolysis thereof.

9 Claims, 1 Drawing Sheet

PROCESS FOR THE SYNTHESIS OF PREGABALIN

TECHNICAL FIELD

The present invention relates to a new process for obtaining pregabalin, i.e. (S)(+)-3-(aminomethyl)-5-methylhexanoic acid of formula (I)

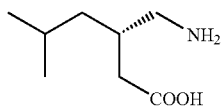

(I)

BACKGROUND ART

Pregabalin is known from U.S. Pat. No. 6,197,819 and is used for treating the peripheral neuropathic pain, epilepsy and anxiety disorders. U.S. Pat. No. 5,637,767 discloses its preparation by classic resolution of the racemate of 3-(aminomethyl)-5-methylhexanoic acid through the formation of diasteroisomeric salts with homochiral acids or bases, separation of the pair of diasteroisomeric salts by fractional crystallization or by crystallography followed by hydrolysis of the salt. However, such process provides pregabalin with low reaction yield with bad effects on the economy of the process, which limit its industrial application. U.S. Pat. No. 6,359,169 discloses its preparation through an enantioselective reaction, using a chiral auxiliary, for example the Evans' oxazolidone (4R,5S)-4-methyl-5-phenyl-2-oxazolidinone, which allows to carry out an asymmetric alkylation in order to insert the desired stereogenic center. After the asymmetric alkylation, generally carried out at cryogenic temperatures, the removal of the comparatively expensive chiral auxiliary is necessary, with a consequent further increase of the costs and of the production time US 2005/0283023 discloses the preparation of pregabalin through kinetic enzymatic resolution of a cyano-diester according to the following scheme:

The above process is commercially practicable, but has noticeable drawbacks, among them the use of pressurized hydrogen for the reduction of the nitrile and the use Nichel Raney, which is toxic and difficult to be used.

*Organic Process Research & Development* 1997; 1: 26-38, discloses another route of synthesis of pregabalin, which makes use of chloroform, which is carcinogenic. Furthermore the last step is carried out in the presence of bromine which is toxic and corrosive and requires special apparatus and precautions.

It has now been found an alternative process for the preparation of pregabalin which overcomes the drawbacks of the above mentioned processes. The new process makes use of inexpensive, low toxic and environmentally friendly reagents and does not requires special apparatus such as cryogenic reactors or high pressure hydrogenators. The new process has been surprisingly found more advantageous than the one disclosed in EP 1 992 609, particularly because it provides greater yields. For the reasons mentioned above the process of the present invention is more suitable for the production on industrial scale.

BRIEF DESCRIPTION OF THE FIGURE AND ANALYSIS METHODS

The crystalline form of Pregabalin has been characterized by X-ray powder diffraction (XRPD), $^1$H-NMR nuclear magnetic resonance spectrometry. The X-ray diffraction spectra (XRPD) were collected with the APD-2000 automatic powder and liquid diffractometer manufactured by Ital-Structures under the following operating conditions: CuKα radiation (λ=1.5418 Å), scanning with a 2θ angle range of 3-40° and a step size of 0.03° for a time of 1 sec. The $^1$H-NMR spectra were acquired with a Varian Mercury 300 spectrometer, using DMSO-d6 as solvent.

FIGURE: XRPD spectrum of crystalline pregabalin.

The particle size and the $D_{50}$ were determined with the known laser light scattering technique, using a Malvern Mastersizer MS1 instrument under the following operating conditions:

300RF mm lens with 2.4 mm laser beam length;
500 mg sample dispersed in 10 ml of hexane (ACS reagent) with 1% of SPAN 85®, without pre-sonication, and with a stirring rate of 2500 rpm.

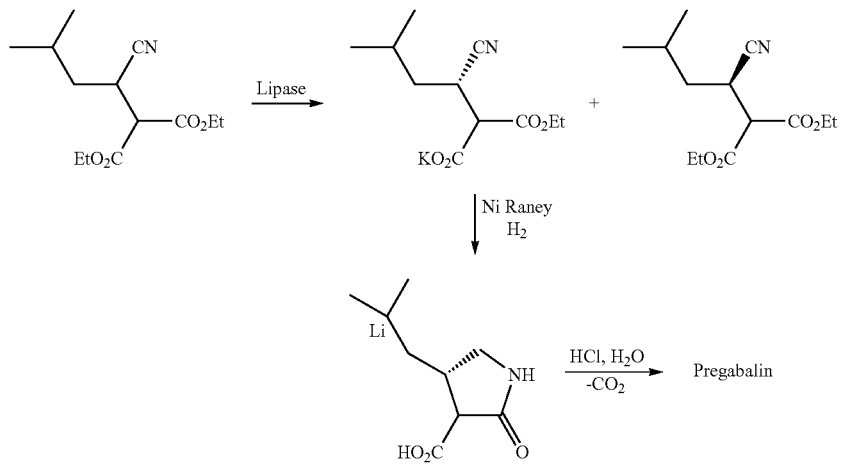

DETAILED DESCRIPTION OF THE INVENTION

The object of this invention is a process for the preparation of (S)(+)-3-(aminomethyl)-5-methylhexanoic acid, of formula (I), or a salt thereof,

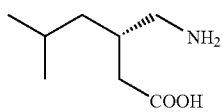
(I)

comprising:
a) the reaction of a compound of formula (II)

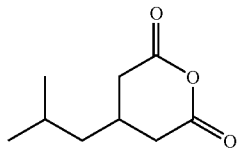
(II)

with zinc azide of formula (III)

$Zn(N_3)_2$ (III)

in the presence of a solvent of formula $R_1$—OH, wherein $R_1$ is an optionally substituted $C_1$-$C_8$ alkyl, aryl or aryl-$C_1$-$C_8$ alkyl group; to obtain a compound of formula (IV)

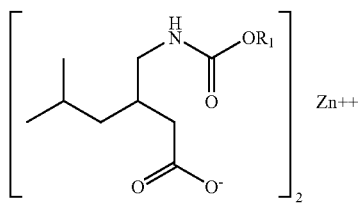
(IV)

wherein $R_1$ is as defined above;
b) its conversion into a compound of formula (V)

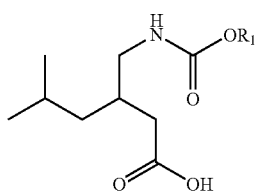
(V)

wherein $R_1$ is as defined above;
c) its enantiomeric enrichment in the (S) enantiomer of formula (VI)

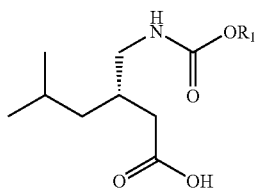
(VI)

wherein $R_1$ is as defined above; and d) the hydrolysis of a compound of formula (VI); and, if desired, the conversion of a compound of formula (I) into a salt thereof, or vice versa.

$R_1$ as $C_1$-$C_8$ alkyl group is preferably a $C_1$-$C_4$ alkyl group, more preferably methyl, ethyl, propyl, i-propyl, butyl, isobutyl, or tert-butyl; more preferably i-propyl. Such alkyl group is optionally substituted by 1 to 5 substituents, preferably 1 or 2, independently selected from halogen, cyano and $C_1$-$C_6$ dialkyl-amino, for example dimethyl-, diethyl-, o diisopropyl-amino.

$R_1$ as aryl group is for example phenyl or naphtyl, in particular phenyl, optionally substituted by 1 to 5 substituents, preferably 1, 2 or 3, independently selected from $C_1$-$C_6$ dialkyl-amino, nitro, cyano and halogen. $R_1$ as aryle-$C_1$-$C_8$ alkyl group is for example, phenyl-$C_1$-$C_6$ alkyl or naphtyl-$C_1$-$C_o$ alkyl, in particular phenyl-$C_1$-$C_4$ alkyl, preferably benzyl or phenylethyl, optionally substituted at the arylic and/or alkylic portion by 1 to 5, preferably 1 or 2, substituents independently selected from halogen, nitro, cyano and $C_1$-$C_6$ dialkyl-amino, for example dimethyl-, diethyl-, or diisopropyl-amino.

A halogen is for example chlorine, fluorine, bromine, iodine, in particular chlorine or bromine.

A group or alkyl residue, as defined above, can be straight or branched.

With reference to this, invention, with the term compound of formula (I) or (V), a compound formula (I) or of formula (V) as such or a salt thereof is intended. Such salt, is preferably a pharmaceutically acceptable one, with a pharmaceutically acceptable acid or base. For example a salt with an inorganic base, such as a lithium, sodium, potassium, magnesium or aluminium salt; or with an organic base, for example methylamine, triethylamine, hydrazine or phenylethylamine; or a salt with an acid selected for example from acetic, hydrochloric, sulphuric, methanesulphonic, propionic and camphorsulphonic acid. Such compounds can be converted into the salts thereof, or vice versa, according to known methods. The compound of formula (II) is known.

The compound of formula (III) is commercially available; however it can also be obtained by in situ reaction of sodium azide anc zinc chloride, according to known methods.

The amount of zinc azide of formula (III) can be approximately comprised between about 1 and 3 moles per mole of substrate of formula (II), preferably between about 1 and about 1.5.

The reaction of a compound of formula (II) and zinc azide can be carried out at a temperature comprised approximately between about 60 and 80° C., preferably between about 70 and 75° C. The reaction time can range between about 2 and about 4 hours.

During the reaction of a compound of formula (II) with a compound of formula (III) an acylazide intermediate, which is not isolated, forms and in the presence of the solvent of formula $R_1$—OH, as defined above, and at the reaction temperature it converts into the compound of formula (IV).

The conversion of a compound of formula (IV) into a compound of formula (V) can be carried out by adding an aqueous solution of a strong protic acid selected from the group comprising hydrochloric, hydrobromic, sulphuric and nitric acid; preferably 37% hydrochloric acid.

A compound of formula (V) can be enantiomerically enriched in the (S) enantiomer of formula (VI) by optical resolution through the formation of a diasteroisomeric salt thereof with a resolving agent, separation of the diasteroisomeric pair by fractional crystallization or by chromatography followed by the cleavage of the salt of the (S) enantiomer of the so formed compound of formula (VI). A diasteroisomeric salt can be formed, for example, by reaction of a compound of formula (V) with a resolving agent, optionally in the presence of a solvent or of an organic base, for example a tertiary amine in particular triethylamine, or both. Said resolving agent can be a chiral base typically a chiral amine, selected, for example, from those mentioned in "S. H. Wilen—*Tables of Resolving Agents and Optical Resolutions*", such as for example brucine, cinchonidine, cinchonine, quinine, strychnine, S-(−)-phenyl-ethyl-amine, S-(−)-naphtyl-ethyl-amine; preferably S-(−)-phenyl-ethyl-amine. A solvent can be, for example, one of the solvents mentioned in step a), or an ester, such as ethyl acetate or methyl acetate; in particular a $C_1$-$C_4$ alkanol for example methanol, ethanol or i-propanol; or a mixture of one or more, preferably two or three of said solvents. Alternately the resolution can be carried out in water or mixtures thereof with one or more of the above mentioned solvents, preferably one or two of the above defined solvents, such as water and alcohol or water and acetone. Preferably the resolution is carried out in water or mixtures of water and a $C_1$-$C_4$ alkanol.

The optical purity of a compound of formula (VI), or of a so obtained diastereoisomeric salt thereof is typically equal to or higher than 98%; preferably equal to or higher than 99%.

Such purity can be optionally increased till it is equal to or higher than 99.9% by known techniques for example by crystallization.

The hydrolysis of a compound of formula (VI) to obtain a compound of formula (I), namely the (S)(+)-3-(aminomethyl)-5-methylhexanoic acid, or a salt thereof, is typically an acidic hydrolysis and can be carried out for example by treatment with a mineral acid, for example sulphuric or hydrochloric acid; in particular concentrated hydrochloric acid.

A compound of formula (I) can be converted into a salt thereof, or vice versa according to known methods.

The so obtained (S)(+)-3-(aminomethyl)-5-methylhexanoic acid has an enantiomeric purity equal to or higher than the enantiomeric purity of the compound of formula (VI) used as intermediate. Thus, using a compound of formula (VI) with high enantiomeric purity, typically equal to or higher than 98%, the process of the invention provides pregabalin with an enantiomeric purity equal to or higher than 99%, which complies with the pharmaceutical regulatory requirements.

The enantiomeric purity is defined as S/(S+R)×100, S and R are respectively the amounts of the enantiomers (S) and (R). According to the invention the term enantiomer (S) or (R) means that the enantiomeric purity is at least, equal to about 96% or higher, preferably at least equal to about 99%.

Pregabalin obtained according to the process of the present invention has a purity equal to or higher than 99.5% preferably equal to or higher than 99.9%, which complies with the regulatory requirements. Pregabalin with such purity is new and is a further object of this invention.

Pregabalin obtained according to the process of this invention has a mean particle size $D_{50}$ comprised between 10 and 250 micrometers, such particle size can be reduced, for example by a process of fine grinding according to known techniques or can be increased checking the crystallization conditions, for example cooling the solution slowly, as it is known.

The crystalline form of pregabalin obtained according to the process disclosed herein shows the most intense peaks at 9.4; 12.2; 14.4; 16.6; 18.2; 19.0; 19.7; 20.1; 22.1; 22.6; 23.1; 23.4; 24.6; 26.8; 27.5; 27.9; 29.8±2θ, as illustrated in FIG. 1, which corresponds to the one disclosed in CN1634869A.

The following examples illustrates the invention.

Example 1

Synthesis of the 3-(isopropoxycarbonylamino-methyl)-5-methyl-hexanoic acid (V; R=isopropyl)

A 1000 ml three-necked round-bottom flask, under nitrogen atmosphere, is added with isopropanol (272 ml), then with zinc chloride (18.1 g, 133 mmoles) and sodium azide (19 g, 293 mmoles). The suspension is stirred at room temperature for 30-40 minutes, then it is brought to 75° C. and 3-isobutyl-glutaric anhydride (45.3 g, 266 mmoles) is dropped therein in about one hour (45.3 g, 266 mmoles), always maintaining the temperature at about 75-80° C. After the adding, the mixture is stirred at such temperature for other 1-2 hours. $H_2O$ (136 ml) and $NaNO_2$ (20.2 g, 293 mmoles) are added, and the mixture is cooled to about −5° C. and, maintaining the temperature lower than 10° C., 37% hydrochloric acid (63 g, 638 mmoles) is dropped therein. At this stage toluene (45 ml) is added, the phases are separated and the aqueous one is extracted with other toluene (20 ml). The organic phases are collected and concentrated under vacuum, providing 58.7 g of an oily residue (yield 90%).

$^1$H-NMR (300 MHz, DMSO-$d_6$, 28° C.): δ 7.00 (broad, 1H changeable with $D_2O$); 4.70 (m, 1H); 3.00 (m, 1H); 2.80 (m, 1H); 2.10 (m, 2H); 1.95 (m, 1H); 1.60 (m, 1H); 1.20-1.00 (m, 8H); 0.80 (d, 6H).

Example 2

Preparation of the (S)-3-(isopropoxycarbonyl-aminomethyl)-5-methyl-hexanoic acid (VI; $R_1$=isopropyl)

A 500 ml three-necked round-bottom flask, under nitrogen atmosphere, is added with raceme 3-(isopropoxycarbonyl-amino-methyl)-5-methyl-hexanoic acid (44.2 g, 0.180 moles), triethylamine (8.20 g, 0.081 moles) and (S)-(−)-phenyl-ethylamine (12.00 g; 0.099 moles) in a 95:5 water/isopropanol mixture (200 ml) heated at 55-60° C. The mixture is spontaneously left to cool to room temperature, then it is cooled to 0-5° C. for at least 1 h. The solid is filtered off and washed with cool water (2×20 ml) and then with cool toluene (4×20 ml), it is dried in oven at 55-60° C. for 16-18 h. 27.0 g of white solid are obtained with an enantiomer ratio of 99:1.

$^1$H-NMR (300 MHz, $CDCl_3$, 28° C.): δ 7.4-7.1 (m, 5H); 4.7 (m, 1H); 4.0 (q, 1H); 3.0 (dd, 1H); 2.8 (dd, 1H); 2.1 (m, 1H); 1.9 (m, 2H); 1.6 (m, 1H); 1.3 (d, 3H), 1.1 (d, 6H); 1.0 (m, 2H); 0.8 (dd, 6H).

Example 3

Synthesis of the (S)-(+)-3-aminomethyl-5-methyl-hexanoic acid (I)

A 500 ml three-necked round-bottom flask, under nitrogen atmosphere, is added with (S)-3-(isopropoxycarbonyl-amino-methyl)-5-methyl-hexanoic acid salt of (S)-(−)-phenyl-ethyl-amine (70.0 g, 0.190 moles), 35% hydrochloric acid (29.7 g, 0.285 moles), water (200 ml) and toluene (100 ml) and the mixture is vigorously stirred for 10-15 minutes. The phases are separated and the aqueous phase is extracted with toluene (2×100 ml). The collected organic phases are concentrated to small volume to obtain an oil which is added with 30% hydrochloric acid (57.8 g, 0.475 moles). The mixture is heated at 90° C. for 24-48 h. At end-reaction 41% aqueous monomethylamine (26.7 ml) is added till pH of about 6 and left to cool to room temperature. The mixture is cooled to 0-5° C. for at least 1 h and then the solid is filtered off and washed with a 1:1 water/isopropanol mixture cooled to 0-5° C. (3×15 ml). The solid is dried in oven at 50-60° C. for 16-18 h. 26.6 g of a white solid are obtained having an enantiomer ratio 99.94:0.06, with a yield of 88%. The XRPD spectrum of the so obtained product has the most intense peaks at 9.4; 12.2; 14.4; 16.6; 18.2; 19.0; 19.7; 20.1; 22.1; 22.6; 23.1; 23.4; 24.6; 26.8; 27.5; 27.9; 29.8±2θ, as illustrated in FIG. 1. The product has a mean particle size $D_{50}$ of about 50 micrometers.

The invention claimed is:

1. Process for the preparation of (S)(+)-3-(aminomethyl)-5-methylhexanoic acid, of formula (I), or a salt thereof,

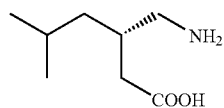
(I)

comprising:
a) the reaction of a compound of formula (II)

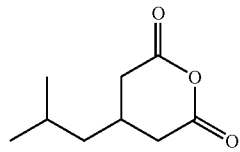
(II)

with zinc azide of formula (III)

(III)

in the presence of a solvent of formula $R_1$—OH, wherein $R_1$ is an optionally substituted $C_1$-$C_8$ alkyl, aryl or aryl-$C_1$-$C_8$ alkyl group; to obtain a compound of formula (IV)

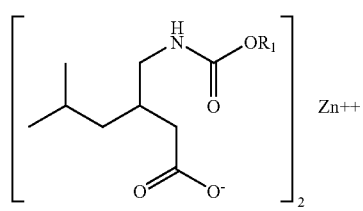
(IV)

wherein $R_1$ is as defined above;

b) its conversion into a compound of formula (V)

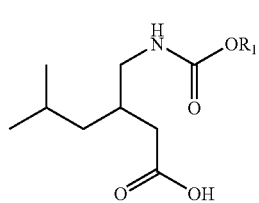
(V)

wherein $R_1$ is as defined above;
c) its enantiomeric enrichment in the (S) enantiomer of formula (VI)

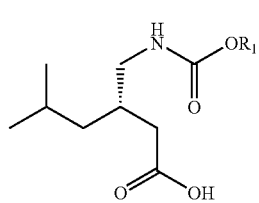
(VI)

wherein $R_1$ is as defined above; and
d) the hydrolysis of a compound of formula (VI); and, if desired, the conversion of a compound of formula (I) into a salt thereof, or vice versa.

2. A process according to claim 1, wherein the amount of zinc azide is approximately comprised between 1 and 3 moles per mole of substrate of formula (II).

3. A process according to claim 1, wherein the amount of zinc azide is comprised between about 1 and about 1.5 moles per mole of substrate of formula (II).

4. A process according to claim 1, wherein in the solvent of formula $R_1$—OH, $R_1$ is a $C_1$-$C_4$ alkyl group.

5. A process according to claim 1, wherein zinc azide is prepared in situ.

6. A process according to claim 1, wherein the enantiomeric enrichment is carried out by optical resolution through the formation of a diasteroisomeric salt of a compound of formula (V) with a resolving agent.

7. A process according to claim 6 wherein, the formation of a diasteroisomeric salt with a resolving agent is carried out in the presence of a solvent and optionally of an organic base.

8. A process according to claim 6, wherein the resolving agent is a chiral base selected from the group comprising brucine, cinchonidine, cinchonine, quinine, strychnine, (S)-(−)-phenyl-ethylamine and S-(−)-naphthyl-ethylamine.

9. A process according to claim 7, wherein the organic base is a tertiary amine.

* * * * *